United States Patent [19]

Blount

[11] 4,032,511
[45] June 28, 1977

[54] PROCESS FOR THE PRODUCTION OF PHENOL SILICATE COMPOUNDS AND THEIR CONDENSATION PRODUCTS

[76] Inventor: David H. Blount, 5450 Lea St., San Diego, Calif. 92105

[22] Filed: Mar. 31, 1976

[21] Appl. No.: 672,559

Related U.S. Application Data

[63] Continuation-in-part of Ser. No. 555,078, March 3, 1975, abandoned.

[52] U.S. Cl. .......................... 260/46.5 R; 260/2 S; 260/18 S; 260/53 R; 260/448.8 R; 423/325
[51] Int. Cl.² ........................................ C08G 77/04
[58] Field of Search ........ 260/448.8 R, 2 S, 46.5 R, 260/53 R, 18 S; 423/325

[56] References Cited

UNITED STATES PATENTS

| | | | |
|---|---|---|---|
| 3,937,782 | 2/1976 | Blount | 423/325 |
| 3,956,466 | 5/1976 | Blount | 423/325 |
| 3,960,747 | 6/1976 | Blount | 423/325 |
| 3,962,067 | 6/1976 | Blount | 423/325 |

*Primary Examiner*—Melvyn I. Marquis

[57] ABSTRACT

Phenol compounds and silicic acids will chemically react to produce a phenol silicate when heated with a suitable alkali catalyst. The phenol silicate compounds are then chemically reacted with an aldehyde to form a condensation product.

16 Claims, No Drawings

PROCESS FOR THE PRODUCTION OF PHENOL SILICATE COMPOUNDS AND THEIR CONDENSATION PRODUCTS

CROSS-REFERENCE TO RELATED CO-PENDING APPLICATION

This application is a continuation-in-part of U.S. patent application Ser. No. 555,078, filed Mar. 3, 1975 now abandoned.

BACKGROUND OF THE INVENTION

This invention relates to a process for the production of phenol silicate resinous compounds by chemically reacting a silicic acid with a phenol compound while heating the mixture in the presence of an alkali catalyst, thereby producting a phenol silicate compound which is then heated with as aldehyde, thereby producing an aldehyde phenol silicate resinous compound.

Various silicic acids may be used in this process such as moist silicic acid gel, air dried silicic acid gel, orthosilicic acid, metasilicic acid, polysilicoformic acid, orthosilicoformic acid, silicoformic acid and monosilandiol. The orthosilicic acid, metasilicic acid and silicic acid gel may be produced by any of the well known methods, such as adding a acid to a solution of sodium metasilicate and precipitating the silicic acid gel.

The orthosilioformic acid, polysilicoformic acid and monosilandiol may be produced by the chemical reaction of a dry alkaline earth metal metasilicate or a dry alkali metal metasilicate with a mineral acid or a hydrogen salt, as disclosed in U.S. patent applications Ser. Nos. 569,952; 600,531; 561,084; 608,724; 612,843; 551,534; 527,906 and 498,045; filed by David H. Blount. Silicoformic acid also known as monosilanic acid, orthosilicoformic acid, polysilicoformic acid and monosilandiol may be produced by other methods such as those disclosed in U.S. Pat. Nos. 3,674,430 and 3,937,782.

Phenol silicate compounds will chemically react with diisocyanate, dicarboxyl acids and anhydrides, ketones, furans and aldehydes to produce useful resinous compounds which may be dissolved in organic solvents such as acetic acid and may be used as a coating agent to protect wood. Phenol silicates may be used as fillers in paints and varnishes. The aldehyde phenol silicate resins may be used as molding powders then heated to the softening point and molded into useful objects such as tool handles, ash trays, etc. The aldehyde phenol silicate resins may be used as casting resins by pouring the said liquid resin into a mold and continuing to heat until an insoluble solid resin is formed, thereby producing a useful object. Solutions of aldehyde phenol silicate resins may be used as adhesives, paints, varnishes, impregnants and laminates.

SUMMARY OF THE INVENTION

I have discovered that silicic acid will react chemically with phenols in the presence of a small amount of alkali catalyst at a temperature just below the boiling temperature of the phenol to produce a phenol silicate when a 1:1 mol ratio is used. When about 2 mols of a phenol are reacted with 1 mol of silicic acid, a diphenol silicate is produced. When 2 mols of silicic acid are reacted with a 1 mol of resorcinol a resorcinol disilicate is produced.

While all of the details of the reactions which take place are not fully understood, it appears that the silicic acid generally reacts with one of the hydroxyl groups of the phenol compound to produce a phenol silicate compound. The reaction is theorized to take place as follows:

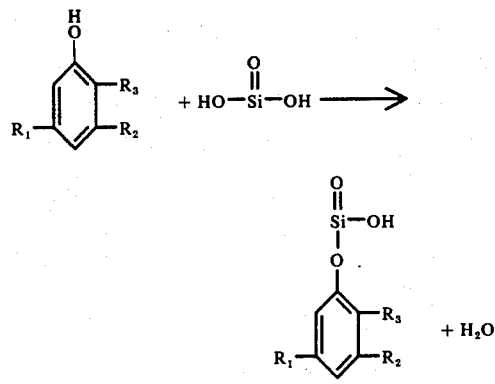

wherein $R_1$, $R_2$, and $R_3$ are selected from the group consisting of hydrogen, hydroxyl radicals, carboxyl radicals, hydrocarbon radicals.

The phenol silicate compounds will further react with organic aldehydes to produce poly(aldehyde phenol silicate) resins.

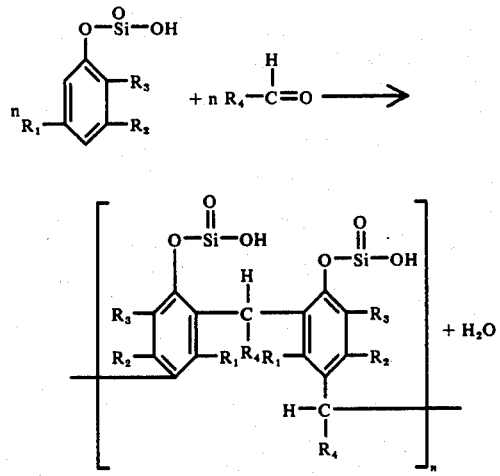

wherein $n$ is a positive integer greater than one; wherein $R_1$, $R_2$, and $R_3$ are chosen from the group consisting of hydrogen, hydroxyl radicals, carboxyl radicals, hydrocarbon radicals. Wherein $R_4$ is chosen from the group consisting of hydrogen, hydrocarbon radicals, benzyl radicals, alkyl radicals, furan radicals, and amine radicals.

DETAILED DESCRIPTION OF THE INVENTION

Any suitable phenol compound may be used in my novel process. Typical phenols include phenol, m-cresol, P-cresol, o-cresol, xylenols, resorcinol, cashew nut shell liquids, anacordol, P-tert-butyl phenol, P-tert-amyl phenol, p-phenyl phenol, cardol, anacardic acid, Bisphenol A, creosote oil, chlorophenol, nitrophenol hydroquinone, pyrogallol and naphthol.

Any suitable alkali catalyst may be used to promote the reaction. The catalytic mechanism which takes place is not fully understood. The alkali may act as a catalyst directly or it may react slightly with one or the other of the primary reactants. From about 1 to 10 weight percent catalyst (based on the weight of the reactants, silicic acid and phenol compound) used gives the best results. Since the alkali can react with the silicic acids and phenol compound, the use of large amounts of alkali should be avoided. Typical alkali includes alkali metal carbonates, hydroxides, oxides and salts of weak acids. The preferred catalyst are the alkali metal carbonates, with best results being obtained with sodium carbonate.

The phenol silicate compounds produced by this method are tan to reddish brown in color, granular, and soften when heated to about 85° C but are destroyed by further heating. The phenol silicate compounds are soluble in aqueous formaldehyde, aldehydes, polyalcohols, acetic acid, acetone, dilute alkali metal solutions, dilute sulfuric acid and other organic solvents.

Various aldehydes may be used to produce poly-(aldehyde phenol silicate) resins such as formaldehyde, acetaldehyde, butylaldehyde, chloral, acrolein, paraformaldehyde, and furfural. The aldehyde ratio may vary from about 0.5 to 3 mols of aldehyde to 1 mol of phenol silicate, depending on the methyol groups desired.

Various catalyst may be used to enhance the reaction between phenol silicate compounds and aldehydes. They may be acidic, basic or neutral. Some of the acid catalysts which may be used are sulfuric acid, sodium hydrogen sulfate, hydrochloric acid, formic acid, acetic acid, oxalic acid, tartaric acid and aromatic sulfonic acid. Some of the basic catalysts are sodium carbonate, sodium silicate, ammonia, sodium hydroxide, potassium hydroxide, calcium hydroxide, urea and quaternary ammonium hydroxide.

DESCRIPTION OF PREFERRED EMBODIMENTS

The following examples describe certain preferred embodiments of the processes which may, of course, be varied as described above with similar results. Parts and percentages are by weight unless otherwise indicated.

EXAMPLE I

About 40 parts by weight of dry granular sodium metasilicate are added to about 100 parts by weight of water to produce an aqueous solution of sodium silicate. Dilute sulfuric acid is added slowly to the solution of sodium silicate until it forms a gel. The silicic acid gel is then washed with water, filtered, and excess water is pressed out of the silicic acid gel.

The said silicic acid gel is mixed with 25 parts by weight of phenol and 3 parts by weight of sodium carbonate and then heated to just below the boiling point of phenol while agitating for 20 to 60 minutes, thereby producing tan granules of phenol silicate.

EXAMPLE II

The tan granules of phenol silicate as produced in Example I are mixed in 75 parts by weight of an aqueous solution containing 37% formaldehyde heated at 65° to 100° C for 10 to 90 minutes while agitating until the desired viscosity is obtained. The tan granules of phenol silicate go into solution and react chemically with the formaldehyde, thereby producing a red resin, poly(formaldehyde phenol silicate). The said resin may be produced in a thick liquid form, in a soft solid resin, or if heating continues, the resin will form a hard insoluble resin. A reflux condenser and a vacuum may be used to remove the water.

The said resin is soluble in acetic acid, except for about 20 to 25% of the silicic acid which was not soluble. A portion of the above 20 to 25% appears to have reacted chemically with the phenol and/or aldehyde to produce a brown resin. The soluble resin turns to a cream color while in an acetic solution. The said solution of poly(formaldehyde phenol silicate) resin may be painted on wood and forms a tough protective coating.

The thick red liquid poly(formaldehyde phenol silicate) resin may be poured into a mold then heated to 60° to 80° C for several hours, depending upon the thickness of the casting, thereby producing hard, tough, useful objects such as gears, art objects, etc.

EXAMPLE III

The tan granules of phenol silicate, as produced in Example I, is mixed with 95 parts by weight of an aqueous solution containing about 37% formaldehyde, and dilute sulfuric acid is added until the pH is about 4 to 5. The mixture is heated to 80° to 100° C while agitating; the phenol silicate goes into solution. The said solution is filtered, and about 15 to 20% of the silicic acid is not soluble. The mixture is then heated to 80° to 100° C while agitating for 20 to 90 minutes or until the desired viscosity is obtained. The cream colored resin may be produced in the form of a thick liquid or a solid resin.

The said resin is soluble in acetic acid, glycerol, vegetable oils, acetone, glycols and other organic solvents. A solution of the said resin may be used as an adhesive to glue wood together and may be used in paints, varnishes and laminates.

The said resin may be used as a molding powder by mixing with hexamethylene tetramine, placing the mixture in a mold, then applying heat at 90° to 110° C following by pressure, thereby producing useful objects which are solid and tough.

EXAMPLE IV

About 20 parts by weight of room air dried silicic acid gel, 20 parts by weight of phenol and 4 parts by weight of potassium carbonate, are mixed, then heated to just below the boiling point of phenol while agitating for 20 to 60 minutes, thereby producing tan granules of phenol silicate.

The said phenol silicate is added to 80 parts by weight of an aqueous solution containing about 37% formaldehyde, then acetic acid is added until the pH is about 5 to 6. The mixture is then heated to 80° to 100° C for 20 to 80 minutes or until the desired viscosity is obtained, thereby producing a cream colored poly(formaldehyde phenol silicate) resin.

The said resin is soluble in acetic acid. The solution of said resin was filtered and about 30 to 40% of the silicic acid was not soluble and was filtered out. A portion of this insoluble silicic acid apparently has reacted with the phenol and/or formaldehyde. The said solution may be used as a coating agent or adhesive on wood.

EXAMPLE V

About 40 parts by weight of dry granular sodium silicate is added to 100 parts by weight of water to produce an aqueous sodium silicate solution; the hydrochloric acid is slowly added while stirring until a silicic acid gel is produced. Sodium carbonate is added until the pH is about 10 to 11, then the silicic acid gel is washed with water, then filtered. Excess water is compressed from the silicic acid gel.

The said silicic acid gel, 25 parts by weight of phenol and 5 parts by weight of dry sodium metasilicate are mixed and heated to just below the boiling point of phenol while agitating for 25 to 75 minutes, thereby producing tan granules of phenol silicate.

The said phenol silicate and 75 parts by weight of an aqueous solution containing about 37% formaldehyde are mixed then heated to 80° to 120° C for 20 to 80 minutes while agitating until the desired viscosity is obtained, thereby producing a red poly(formaldehyde phenol silicate) resin. The resin may be produced as a thick liquid, as a soft resin, or on further heating the said resin will become hard and insoluble in most solvents.

The soft red poly(formaldehyde phenol silicate) resin is soluble in acetic acid, and in an acid solution the said resin turns to a cream color. The soft red resin may be used as a molding resin by adding an acid compound until the pH is 5 to 6, placed in a mold, heated to the softening point and then compressed, thereby producing light, tan, hard, tough useful objects.

EXAMPLE VI

Moist silicic acid gel, equivalent to 25 parts by weight of dry silicic acid gel, about equal parts by weight of phenol and 3 parts by weight of sodium carbonate are mixed, then heated to just below the boiling point of phenol while agitating for 20 to 80 minutes, thereby producing tan granules of phenol silicate.

About 25 parts by weight of furfural and about 3 parts by weight of sodium hydroxide granules are added to the said phenol silicate, mixed then heated to just below the boiling point of furfural for 10 to 50 minutes until the desired viscosity is obtained, thereby producing brown poly(furfural phenol silicate) resin. The said resin may be produced as a thick brown liquid, brown fusable solid, or infusable solid, depending on the length of time that the resin is heated.

Poly(furfural phenol silicate) resin is soluble in acetic acid, acetone, polyalcohols, oils and other organic solvents. About 15 to 20% of the silicic acid gel is not soluble in organic solvents. A solution of the said resin may be used as a protective coating on wood. The thick brown liquid resin may be cured to produce a hard tough solid resin by the addition of a mineral acid until the pH is 4 to 5.

EXAMPLE VII

Moist silicic acid gel, equivalent to about 25 parts of dry silicic acid gel, about 25 parts by weight of phenol, 25 parts by weight of furfural and 5 parts by weight of sodium carbonate are mixed then heated to just below the boiling point of phenol for 20 to 80 minutes while agitating until the desired viscosity is obtained, thereby producing a brown poly(furfural phenol silicate) resin.

EXAMPLE VIII

Moist silicic acid gel, equivalent to about 10 parts by weight of dry silicic acid gel, about equal parts by weight of cresylic acid and 2 parts by weight of sodium carbonate are mixed then heated to just below the boiling point of cresylic acid for 20 to 60 minutes, thereby producing light brown granules of phenol silicate and cresol silicate.

25 parts by weight of an aqueous solution containing 37% formaldehyde is added to the above mixture, then heated to 80° to 120° C for 20 to 90 minutes while agitating until the desired viscosity is obtained, thereby producing a reddish brown poly(formaldehyde phenol silicate cresol silicate) resin. The resin may be produced as a thick, reddish brown liquid or a reddish brown solid. The said resin is soluble in acetic acid, and upon filtering, one to two parts of the silicic acid is not soluble in acetic acid. A solution of said resin may be used as an adhesive to glue wood together.

EXAMPLE IX

The light brown granules of phenol silicate and cresol silicate as produced in Example VIII are added to 25 parts by weight of an aqueous solution containing about 37% formaldehyde.

Sodium hydrogen sulfate is added to said mixture until the pH is 6 to 7, then the mixture is heated to 80° to 120° C while agitating until the phenol and cresol silicate goes into solution. The solution is heated until the desired viscosity is obtained, thereby producing light brown, solid poly(formaldehyde phenol silicate cresol silicate) resins. The said resin softens with heat and is soluble in acetic acid, acetone, polyalcohols and other solvents.

EXAMPLE X

Moist metasilicic acid equivalent to 20 parts by weight of dry metasilicic acid, 20 parts by weight of cresol(UPS) and 3 parts by weight of sodium hydroxide and mixed, then heated to just below the boiling point of cresol for 20 to 90 minutes, thereby producing cresol silicate which is added to 80 parts by weight of an aqueous solution containing about 37% formaldehyde, heated to 80° to 120° C while agitating for 20 to 90 minutes until the desired viscosity is obtained, thereby producing a light brown poly(formaldehyde cresol silicate) resin.

The said resin may be produced as a thick liquid, soft solid, or a hard solid resin. The said resin is soluble in acetic acid, acetone polyalcohols and other solvents. A solution of said resin may be painted on wood, and it forms a good protective coating. About 10 to 15% of the silicic acid is not soluble in acetic acid.

EXAMPLE XI

The cresol silicate, as produced in Example X, is added to 60 parts by weight of an aqueous solution containing 37% formaldehyde, mixed, then acetic acid is added until the pH is 5 to 6. The said mixture is then heated to 80° to 120° C for 20 to 90 minutes, thereby producing a brown poly(cresol silicate) resin. The resin softens with heat, may be molded and is soluble in acetic acid. About 10 to 15% of the silicic acid is not soluble in acetic acid.

EXAMPLE XII

Moist orthosilicic acid, equivalent to 20 parts by weight of dry metasilic acid, equal parts by weight of creosote oil and 4 parts by weight of sodium metasilicate granules are mixed, then heated to 100° to 160° C while agitating for 20 to 60 minutes, thereby producing brown granules of creosote silicate.

The creosote silicate is added to 60 parts by weight of an aqueous solution containing about 37% formaldehyde, then heated to 80° to 120° C while agitating for 20 to 80 minutes, thereby producing a brown poly(formaldehyde creosote silicate) resin. The said resin is soluble in acetic acid and about 10 to 15% of the silicic acid is not soluble in acetic acid.

EXAMPLE XIII

One mol of concentrated sulfuric acid is slowly added to about 1 mol of granular of sodium metasilicate while agitating and keeping the temperature below 100° C at ambient pressure. Oxygen is evolved, thereby producing a white granular mixture of polysilicoformic acid, orthosilicoformic acid, silicoformic acid, metasilicic acid and sodium sulfate. The white granular mixture is washed with water and filtered to remove the sodium sulfate and then air dried at 25° to 75° C.

One mol of phenol is mixed with the above silicic acids and about 0.2 mol of sodium carbonate is added. The mixture is then heated to 60° to 100° C for 20 to 50 minutes while agitating at ambient pressure, thereby producing tan granules of phenol silicate and phenol silicoformate.

One mol of an aqueous solution of formaldehyde is added to said phenol silicate and phenol silicoformate then heated to 70° to 100° C for 20 to 90 minutes while agitating until the desired viscosity is obtained, thereby producing poly(formaldehyde phenol silicate phenol silicoformate) resin. The red resin may be produced as a thick liquid, soft solid, or a hard solid. In an acid pH, the resin is a cream color. The resin is soluble in acetic acid and other organic solvents, and a solution may be painted on wood and used as an adhesive or a protective coating.

EXAMPLE XIV

The phenol silicate and phenol silicoformate as produced in Example XIII is added to about 1.5 mols of formaldehyde in an aqueous solution. Hydrochloric acid is added to the solution until the pH is about 3 to 5. The mixture is then heated at 70° to 110° C for 20 to 60 minutes at ambient pressure until the desired viscosity is obtained, thereby producing a cream colored poly(formaldehyde phenol silicate phenol silicoformate) resin. The resin may be produced as a thick liquid, soft solid or a hard solid. The thick liquid may be used as an adhesive in the production of laminated wood, paper, etc., and may be cured by heat pressure.

EXAMPLE XV

About 1 mol of dry granular sodium metasilicate is slowly and gradually added to about 1 mol of concentrated sulfuric acid while agitating at ambient pressure and keeping the temperature below 100° C. Oxygen evolves from the mixture. The reaction is complete in 2 to 4 hours, thereby producing silicoformic acid and sodium sulfate. The mixture is washed with water then filtered, thereby removing the salt and recovering the white granular silicoformic acid (H.SiO.OH).

20 parts by weight of silicoformic acid, 25 parts by weight of cresol (USP) and 3 parts by weight of sodium carbonate are mixed then heated to 50° to 95° C for 15 to 45 minutes while agitating at ambient pressure, thereby producing cresol silicoformate, a light brown, granular compound.

The cresol silicoformate is added to 50 parts by weight of an aqueous solution containing about 37% formaldehyde then heated to 70° to 100° C for about 20 to 60 minutes, thereby producing a brown poly(cresol silicoformate) resin. The resin may be produced as a thick liquid, soft solid or a hard solid. The resin is soluble in polyalcohols, acetic acid, acetone and other organic solvents. A solution of said resin may be painted on wood and forms a protective coating for wood.

EXAMPLE XVI

The cresol silicoformate produced in Example XV is added to 60 parts by weight of an aqueous solution containing about 37% formaldehyde, then dilute sulfuric acid is added until the pH is 5 to 6. The mixture is heated to 60° to 90° C for about 20 to 25 minutes while agitating at ambient pressure, thereby producing light brown poly(formaldehyde cresol silicoformate) resin.

EXAMPLE XVII

One mol of dry granular sodium metasilicate is added slowly to 2 mols of concentrated sulfuric acid while agitating at ambient pressure and keeping the temperature below 100° C; oxygen is given off, thereby producing silicoformic acid and sodium hydrogen sulfate. Sodium carbonate is added to the mixture of silicoformic acid and sodium hydrogen sulfate until the pH is about 7, thereby producing monosilanal ($H_2SiO$) and sodium sulfate. The mixture is washed with water and water reacts with monosilanal to produce monosilandiol ($H_4SiO_2$), a white granular compound. The water is filtered off, removing the sodium sulfate and recovering the monosilandiol. The method to produce monosilandiol may also be found in U.S. Pat. No. 3,937,782 and in U.S. patent application Ser. No. 498,045.

One mol of monosilandiol, 1 mol of phenol and 0.2 mol of potassium hydroxide are mixed then heated to just below the boiling point of phenol while agitating at ambient pressure for 15 to 60 minutes, thereby producing phenol monosilandiol, a tan granular compound. The phenol monosilandiol is mixed with about 1 mol of formaldehyde in an aqueous solution, then heated to 70° to 90° C for 20 to 100 minutes until the desired viscosity is obtained, thereby producing poly(formaldehyde phenol monosilandiol) resin. The resin may be produced as a thick liquid, soft solid or a hard solid. The resin is soluble in acetic acid, acetone and other organic solvents, and a solution of the resin may be used as an adhesive or coating on wood.

EXAMPLE XVIII

Phenol monosilandiol as produced in Example XVII is mixed with about 2 mols of formaldehyde in an aqueous solution then oxalic acid is added until the pH is 5 to 6. The mixture is heated to 70° to 100° C for 20 to 80 minutes at ambient pressure while agitating, thereby producing cream colored poly(formaldehyde phenol monosilandiol) resin. The resin is soluble in acetic acid.

EXAMPLE IXX

Moist silicic acid gel, equivalent to 20 parts by weight of dry silicic acid gel, 20 parts by weight of resorcinol and 2 parts by weight of sodium carbonate are mixed then heated to above the melting point and below the boiling point of resorcinol for 15 to 100 minutes while agitating at ambient pressure, thereby producing a resorcinol silicate, a brown granular compound.

The resorcinol silicate is added to 30 parts by weight of an aqueous solution, containing about 37% formaldehyde then heated to 75° to 110° C for 20 to 60 minutes until the desired viscosity is obtained, thereby producing a reddish brown poly(formaldehyde resorcinol silicate) resin. It may be produced as a thick liquid or a solid. The resin may be used as an adhesive on wood and cured by paraformaldehyde or heat.

EXAMPLE XX

Moist silicic acid gel, equivalent to 20 parts by weight of dry silicic acid gel, about equal parts by weight of phenol and 3 parts by weight of sodium carbonate are heated to just below the boiling point of phenol for 20 to 60 minutes, thereby producing tan granules of phenol silicate. The phenol silicate is mixed with 20 parts by weight of crotonaldehyde then heated to 70° to 90° C while agitating under ambient pressure for 20 to 70 minutes, thereby producing a yellow poly(crotonaldehyde phenol silicate) resin. The resin is soluble in acetic acid.

EXAMPLE XXI

The tan granules of phenol silicate as produced in Example XX is added to 20 parts by weight of acrolein then heated to just below the boiling point of acrolein for 20 to 80 minutes thereby producing poly(acrolein phenol silicate) resin.

EXAMPLE XXII

The tan granules of phenol silicate as produced in Example XX is added to about 20 parts by weight of furfural. Dilute sulfuric acid is added to the mixture until the pH is about 4 to 5 while agitating for 5 to 20 minutes, thereby producing poly(furfural phenol silicate) resin.

Although certain specific preferred ingredients and conditions are described in conjunction with the above detailed description of the invention and Examples, these may be varied and other ingredients may be used where suitable, with similar results. For example, various cross-linking or modifying agents may be used.

Other applications, modifications and ramifications of this invention will occur to those skilled in the art upon reading this disclosure. These are intended to be included within the scope of this invention, as defined in the appended claims.

I claim:

1. The process for the production of phenol silicate compounds and their resinous products by the following steps:
   a. mixing about equal parts by weight of silicic acid and a phenol compound;
   b. adding an alkali catalyst equal to 1 to 10% by weight of silicic acid and phenol compound;
   c. heating said mixture to just below the boiling point of the phenol compound for 15 to 100 minutes while agitating, thereby
   d. producing a granular phenol silicate compound.

2. The method of claim 1 wherein the silicic acid is selected from the group consisting of air dried silicic acid gel, moist silicic acid gel, orthosilicic acid, metasilicic acid, polysilicoformic acid, orthosilicoformic acid, silicoformic acid, monosilandiol and mixtures thereof.

3. The method of claim 1 wherein the phenol compound is selected from the group consisting of phenol, p-cresol, o-cresol, m-cresol, cresylic acid, xylenols, resorcinol, cashew-nut shell liquids, anocordol, p-tert-butyl phenol, cardol, anacardic acid, Bisphenol A, creosote oil, 2,6-dimethylphenol, and mixtures thereof.

4. The method of claim 1 wherein the alkali catalyst is selected from the group consisting of sodium carbonate, potassium hydroxide, sodium hydroxide, potassium carbonate, sodium metasilicate and mixtures thereof.

5. The method of claim 1 including the further steps of:
   a. adding an aldehyde in the ratio of 0.5 to 3 mols of each mol of the phenol compound;
   b. heating said mixture to 70° to 110° C for 20 to 80 minutes while agitating, thereby
   c. producing a poly(aldehyde phenol silicate) resin.

6. The method of claim 5 wherein the aldehyde is selected from the group consisting of formaldehyde, acetaldehyde, butylaldehyde, acrolein, paraformaldehyde, furfural, and mixtures thereof.

7. The method of claim 5 including the further step of adding an acid catalyst until the pH is 4 to 6 following step (a) and before step (b).

8. The method of claim 7 wherein the acid catalyst is selected from the group consisting of sulfuric acid, hydrochloric acid, acetic acid, formic acid, oxalic acid, aromatic sulfonic acid, sodium hydrogen sulfate and mixtures thereof.

9. The method of claim 1 wherein the phenol compound is phenol.

10. The method of claim 5 wherein the aldehyde is formaldehyde in an aqueous solution.

11. The process for the production of phenol silicate compounds and their resinous products by the following steps:
    a. providing silicic acid selected from the group consisting of air dried silicic acid gel, moist silicic acid gel, orthosilicic acid, metasilicic acid, polysilicoformic acid, orthosilicoformic acid, silicoformic acid, monosilandiol and mixtures thereof;
    b. providing a phenol compound selected from the group consisting of phenol, p-cresol, o-cresol, m-cresol, cresylic acid, xylenols, resorcinol, cashew nut shell liquids, anacordol, p-tert-butyl phenol, p-tert-amyl phenol, p-phenyl cardol, anacardic acid, Bisphenol A, cresote oil, 2,6-dimethylphenol and mixtures thereof;
    c. mixing said silicic acid and phenol compound in about equal parts by weight;
    d. adding an alkali catalyst selected from the group consisting of sodium carbonate, potassium carbonate, sodium hydroxide, potassium hydroxide, and mixtures thereof, equal to 1 to 10% by weight of silicic acid and phenol compounds;
    e. adding an aldehyde to said mixture ratio of 0.5 to 3 mols to each mol of the phenol compound, and the aldehyde is selected from the group consisting of formaldehyde in an aqueous solution, acetaldehyde, butylaldehyde, acrolein, paraformaldehyde, furfural, and mixtures thereof;
    f. heating said mixture to 70° to 110° C for 20 to 80 minutes while agitating, thereby
    g. producing a poly(aldehyde phenol silicate) resin.

12. The method of claim II wherein in step (f) an acid selected from the group consisting of sulfuric acid, hydrochloric acid, acetic acid, formic acid, oxalic acid, aromatic sulfonic acid, sodium hydrogen sulfate and mixtures thereof, is added to said mixture until the pH is about 3 to 5.

13. The method of claim 1 wherein the silicic acid is selected from the group consisting of air dried silicic acid gel, moist silicic acid gel, orthosilicic acid and metasilicic acid.

14. The method of claim 1 wherein the alkali catalyst is an alkali metal carbonate selected from the group consisting of sodium carbonate and potassium carbonate.

15. The method of claim 11 wherein the silicic acid is selected from the group consisting of air dried silicic acid gel, moist silicic acid gel, orthosilicic acid and metasilicic acid.

16. The method of claim 11 wherein the alkali catalyst is an alkali metal carbonate selected from the group consisting of sodium carbonate and potassium carbonate.

* * * * *